(12) United States Patent
Spitz et al.

(10) Patent No.: US 6,362,471 B1
(45) Date of Patent: Mar. 26, 2002

(54) DESIGN OF A CALIBRATION PHANTOM FOR IN VIVO MEASUREMENT OF STABLE LEAD OR RADIOACTIVITY IN BONE

(75) Inventors: Henry B. Spitz, Cincinnati; Mark Jenkins, Franklin, both of OH (US); Robert Bornschein, Park Hills, KY (US); Jeffrey Lodwick, Franklin, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 09/312,242

(22) Filed: May 14, 1999

Related U.S. Application Data

(60) Provisional application No. 60/085,491, filed on May 14, 1998.

(51) Int. Cl.$^7$ .................................................. A61B 6/00
(52) U.S. Cl. ..................................... 250/252.1; 378/207
(58) Field of Search ........................ 378/207; 250/252.1

(56) References Cited

U.S. PATENT DOCUMENTS

| | | | | |
|---|---|---|---|---|
| 4,577,338 A | * | 3/1986 | Takahashi et al. | 378/48 |
| 4,663,772 A | * | 5/1987 | Mattson et al. | 378/18 |
| 4,845,729 A | * | 7/1989 | Rosen et al. | 378/45 |
| 4,873,707 A | * | 10/1989 | Robertson | 378/18 |

OTHER PUBLICATIONS

Hu et al, Effect of Repeated Occupational Exposure to Lead, Cessation of Exposure, and Chelation on Levels of Lead in Bone, American Journal of Industrial Medicine, 20:723–735 (1991).

Richard P. Wedeen, In Vivo Tibial XFR Measurement of Bone Lead, Archives of Environmental Health, 43: 69–71 (1990).

Andrew C. Todd et al, Workshop on the X–Ray Fluorescence of Lead in Bone: Conclusions, Recommendations and Summary, Neuro Toxicology 14: 145–154 (1993).

(List continued on next page.)

Primary Examiner—Constantine Hannaher
(74) Attorney, Agent, or Firm—Frost Brown Todd LLC

(57) ABSTRACT

The hazards of exposure to heavy metal contamination, examples of which arsenic, beryllium, lead, cadmium, chromium, nickel, zinc, mercury and barium, and the radioactive substances which deposit in human bone, examples of which are uranium, plutonium, and americium, are very serious and are well known to scientific and medical professionals. Since lead is a prevalent metal contaminant which deposits in human bone, and its effects are quite hazardous, especially to young children, the focus of this disclosure will be on methods of detecting lead exposure. While it is possible to detect the level of lead in the body through the use of a blood test, the relevancy of such tests is limited, since the risk to humans from lead exposure is related to the amount of lead deposited in the bones of the exposed person and not, necessarily, the amount in the blood. Moreover, drawing blood causes some discomfort on the part of the person being tested, which is especially difficult with small children, who are particularly at risk to lead exposure due to various environmental factors. Accordingly, an alternative method, the indirect measure of the level of cumulative lead exposure in the bones of a person by sue of x-ray fluorescence, is often employed. This invention relates generally to surrogate structures, or phantoms, that exhibit radiological properties of bone, muscle, and other soft tissue. Specifically, this invention relates to phantoms which have been designed to accurately exhibit anthropometric and radiological properties of human bone and soft tissue for use in calibrating the response of spectroscopic instruments that enable in vivo measurement of the levels of contamination from stable metals and radioactive material.

22 Claims, 4 Drawing Sheets

OTHER PUBLICATIONS

Howard Hu et al, X–Ray Fluorescence Measurements of Lead Burden in Subjects with Low–Level Community Lead Exposure, Archives of Environmental Health, 45: 335–341 (1990).

Howard Hu et al, The Use of K X–Ray Fluorescence for Measuring Lead Burden in Epidemiological Studies: High and Low Lead Burdens and Measurement Uncertainty, Environmental Health Perspectives, 94: 107–110 (1991).

Jane A. Hoppin et al, In Vivo Bone Lead Measurement in Suburban Teenagers, Pediatrics, 100: 365–370 (1997).

D.R. Chettle et al, Lead in Bone: Sampling and Quantitation Using K X–Rays Excited by $^{109}$Cd, Environmental Health Perspectives, 91: 49–55 (1991).

Hirokastsu Watanabe et al, Correlates of Bone and Blood Leads Levels in Carpenters, American Journal of Industrial Medicine, 26: 255–264 (1994).

Lillian J. Somervaille et al, In Vivo Measurement of Lead in Bone Using X–Ray Fluorescence, Phys. Med. Biol., 10: 929–943 (1985).

Mauricio Hernandez–Avila et al, The Influence of Bone and Blood Lead on Plasma Lead Levels in Environmentally Exposed Adults, Environmental Health Perspectives, 106: 473–477 (1998).

A C A Aro et al, Improvements in the Calibration of $^{109}$Cd K X–Ray Fluorescence Systems for Measuring Bone Lead in Vivo, Phys. Med. Biol., 39:2263–2271 (1994).

Andrew Christian Todd et al, In Vivo X–Ray Fluorescence of Lead in Bone, Environmental Research, 59: 326–335 (1992).

D.R. White, Tissue Substitutes in Experimental Radiation Physics, Med. Phys., 5: 467–479 (1978).

A.J. Stacey et al, A New Phantom Material Employing Depolymerised Natural Rubber, 34: 510–515 (1961).

John H. Harris, Jr., et al, The Development of a Chest Phantom For Use in Radiologic Dosimetry, Radiology, 67: 805–813(1956).

R.V. Griffith et al, Fabrication of a Tissue–Equivalent Torso Phantom for Intercalibration of In–Vivo Transuranic–Nuclide Counting Facilities, presented at Symposium on Advances on Radiation Protection Monitoring, Stockholm, 1978.

* cited by examiner

DESIGN OF A CALIBRATION PHANTOM FOR IN VIVO MEASUREMENT OF STABLE LEAD OR RADIOACTIVITY IN BONE

This is a non-provisional application based upon an earlier filed provisional application, Ser. No. 60/085,491, filed May 14, 1998.

The U. S. Government has a paid-up license in this invention and the right in limited circumstances to require patent owner to license others on reasonable terms as provided for by the terms of Grant/Contract No. GM47122, awarded by the National Institutes of Health.

FIELD OF THE INVENTION

This invention relates generally to surrogate structures, or phantoms, that exhibit radiological properties of bone, muscle, and other soft tissue. Specifically, this invention relates to phantoms which have been designed to accurately exhibit anthropometric and radiological properties of human bone and soft tissue for use in calibrating the response of spectroscopic instruments that enable in vivo measurement of the levels of contamination from stable metals and radioactive material.

BACKGROUND OF THE INVENTION

The hazards of exposure to heavy metal contamination, examples of which arsenic, beryllium, lead, cadmium, chromium, nickel, zinc, mercury and barium, and the radioactive substances which deposit in human bone, examples of which are uranium, plutonium, and americium, are very serious and are well known to scientific and medical professionals.

Since lead is a prevalent metal contaminant which deposits in human bone, and its effects are quite hazardous, especially to young children, the focus of this disclosure will be on methods of detecting lead exposure. While it is possible to detect the level of lead in the body through the use of a blood test, the relevancy of such tests is limited, since the risk to humans from lead exposure is related to the amount of lead deposited in the bones of the exposed person and not, necessarily, the amount in the blood. Moreover, drawing blood causes some discomfort on the part of the person being tested, which is especially difficult with small children, who are particularly at risk to lead exposure due to various environmental factors Accordingly, an alternative method, the indirect measure of the level of cumulative lead exposure in the bones of a person by use of x-ray fluorescence, is often employed.

By way of example, by directing a source of radiation, such as gamma rays from a $^{109}$Cd source, through a portion of the human body, such as the midshaft of the tibia, a suitable detector is capable of providing a calcium to lead ratio in the bone by comparing the intensity of the Pb x-rays caused by the interaction with the $^{109}$Cd photons to the intensity of the back scattered photons caused by the interactions of the $^{109}$Cd photons with the calcium atoms in the bone.

The accuracy of the lead measurements given by this method, especially when the levels of lead exposure are low, is questionable for two reasons: first, because it relies on an assumed calcium content in the particular bone, which may or may not be accurate in individual cases, and second, since there is a wide diversity in skeletal size in humans, as well as differences in the amount of tissue surrounding the bone that the x-rays must pass through and be partially absorbed by, these differences have to be taken into account for the x-ray source to be calibrated correctly.

While cadaver samples are the most realistic calibration structures to use, limitations on availability generally require the use of surrogate structures, or phantoms, in making calibration measurements. Currently, such phantoms are 4" long, cylindrical structures made of either Plaster of Paris or polyacrylamide. Neither of these materials is an acceptable, realistic substitute for human bone. Moreover, these conventional phantoms do not account for the x-ray attenuation caused by the layers of tissue overlying the bone being tested by this method. These concerns also hold for the other metal contaminants, such as mercury, that would be tested for by means of x-ray fluorescence.

It is well-known by those skilled in the art that, when testing to determine the amount of a radioactive contaminant that has been deposited in bone, gamma spectrometry is the usual analytical tool. Since the above-mentioned prior art phantom is also used in gamma spectrometry measurements, the same concerns apply.

There is, therefore, a substantial need for an improved phantom representative of tissue-covered human bone containing lead in a long-term, stable format, and a low cost method of quantifying human bone lead content which is fast, accurate, reproducible, and widely available.

BRIEF SUMMARY OF THE INVENTION

Pursuant to the present invention, a method of making anthropomorphically correct phantom structures will be provided.

Also pursuant to the present invention, a method of using these anthropomorphically correct phantom structures will be provided.

It is an object of the present invention to provide a phantom allowing direct measurement of the amount of radioactive or heavy metal contaminants deposited in a particular human bone.

It is another object of the present invention to provide an anthropomorphically correct phantom structure that is designed from commonly available materials, is easily reproducible, and is capable of widespread availability and usage.

Additional objects, advantages, and novel features of the present invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

Other features and advantages of the present invention will appear from the following description of a particular exemplary embodiment, said description being made with reference to the appended drawings wherein.

DETAILED DESCRIPTION OF THE INVENTION

Figure 1:
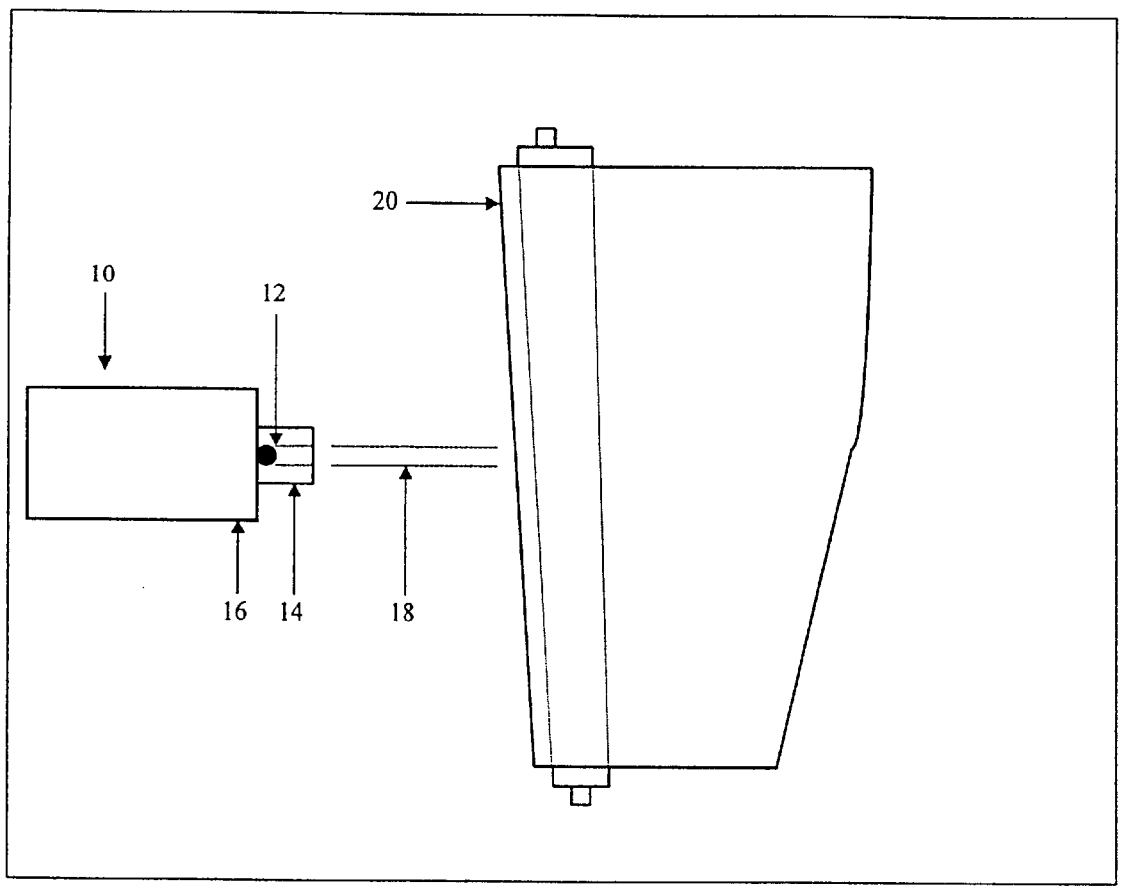
FIG. 1 is a side view showing the use an x-ray fluorescence detector system with an embodiment of the present invention.

By reference to the drawings, the best mode of using the preferred embodiment of the present invention will be described. Now making reference to FIGS. 1 and 2, the operation of an x-ray fluorescence detector system will be described. The detector system (10) consists of a photon source (12) and a photon shield (14) in connection with an x-ray detector (16) that measures the response to a photon beam (18) emitted by the photon source (12). The photon beam (18), typically generated from a $^{109}$Cd source (12) emitting photons of approximately 88 keV in energy, is directed onto the calibration phantom (20), which is anthropomorphically shaped to resemble the mid-shaft of the lower leg of a human (not shown). The detector (16) measures the quantity of photons and x-rays produced in the phantom, caused by interactions with calcium and metals in the phantom, and scattered towards the detector.

Figure 3:
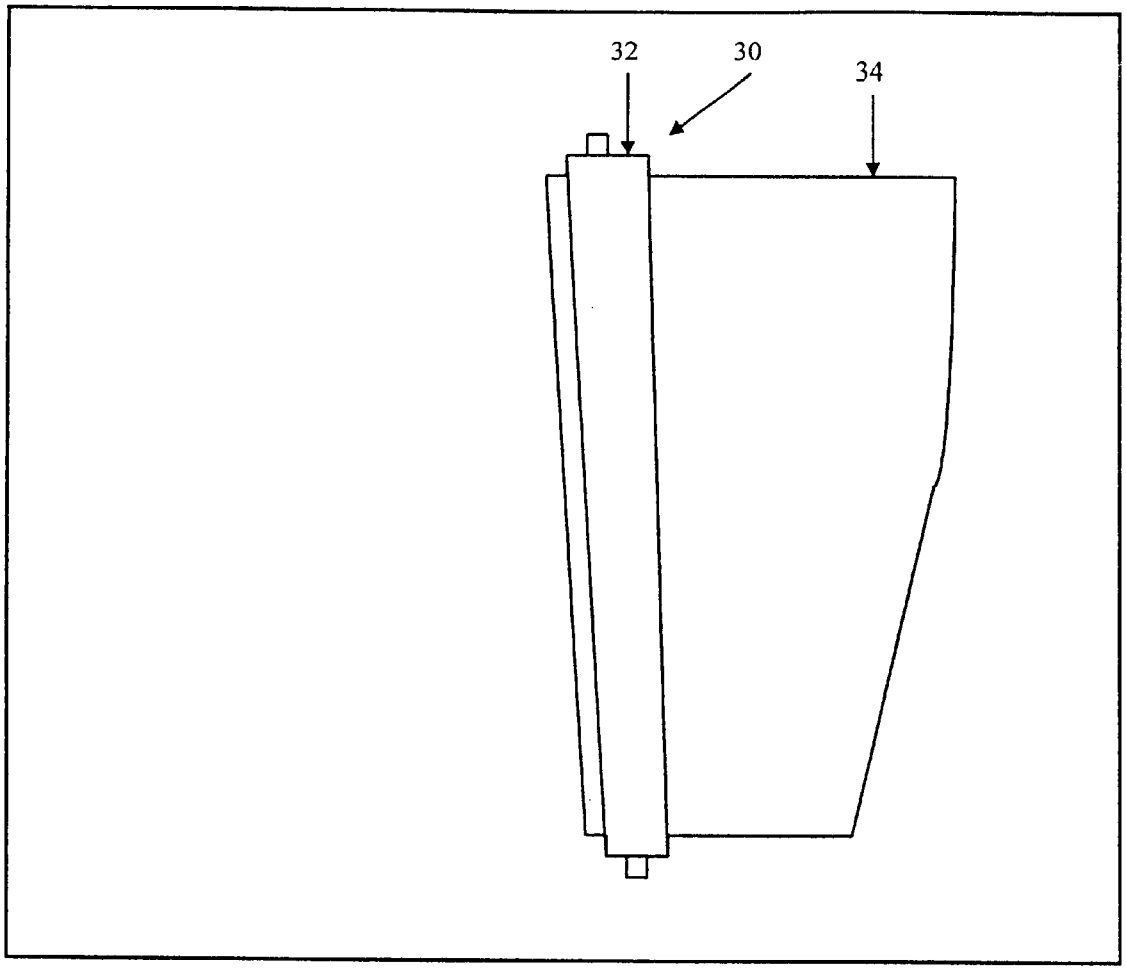
FIG. 3 is a cut-away view of an embodiment of the present invention, showing a muscle simulant and a bone structure.
Figure 4:
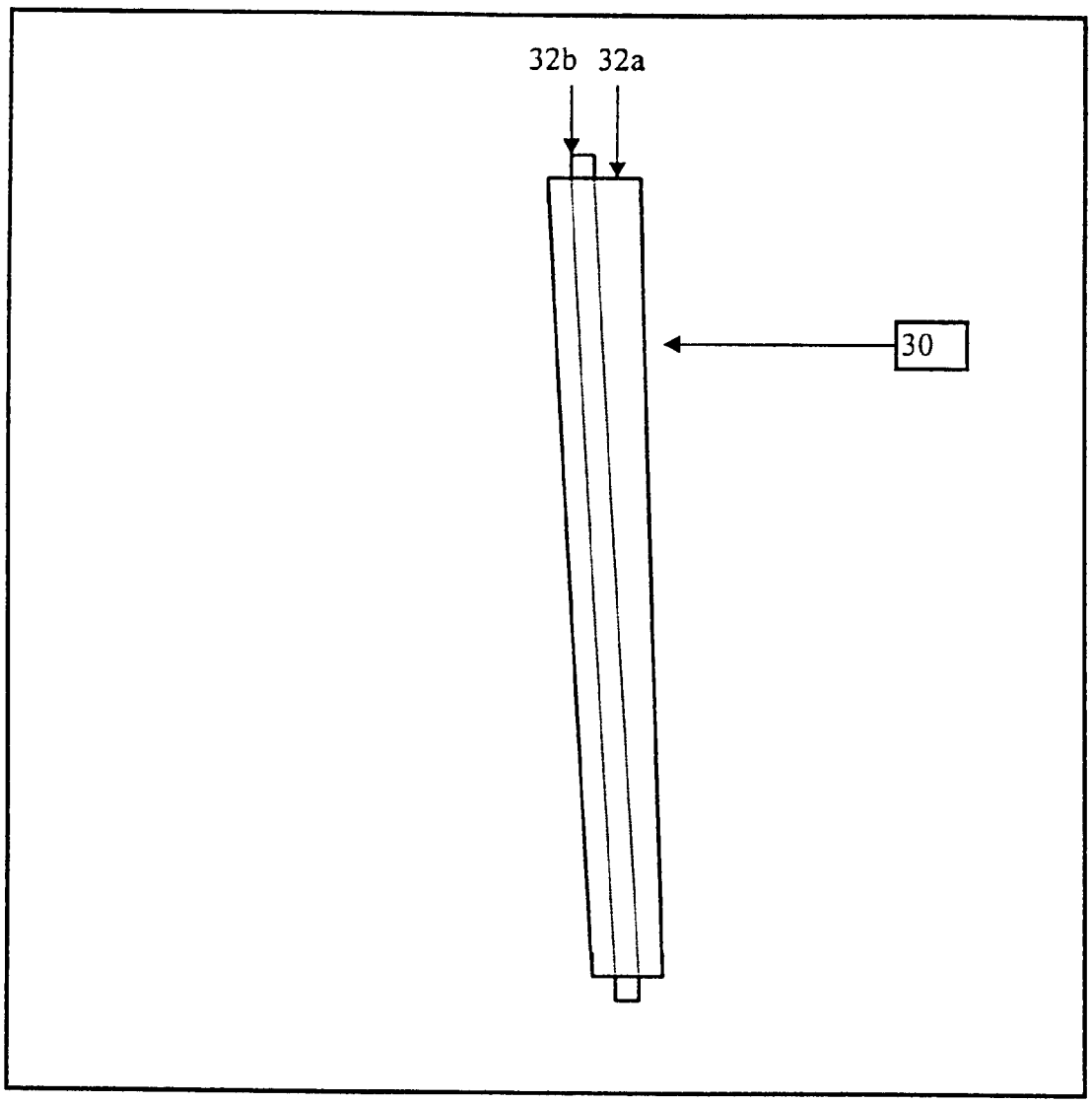
FIG. 4 is a cut-away view of an embodiment of the present invention, showing the cortical bone section and the bone marrow section.

Now making reference to FIGS. 3 and 4, the structure of an embodiment of the present invention is shown in detail. A tibia phantom (30) having a surrogate tibia bone (32) surrounded by muscle simulant (34) and having the anthropomorphic shape of a lower leg is shown. The bone structure (32) has two major components: an outer bone simulant structure (32a), which in this embodiment is meant to simulate cortical bone, and a bone marrow simulant structure (32b).

Figure 2:
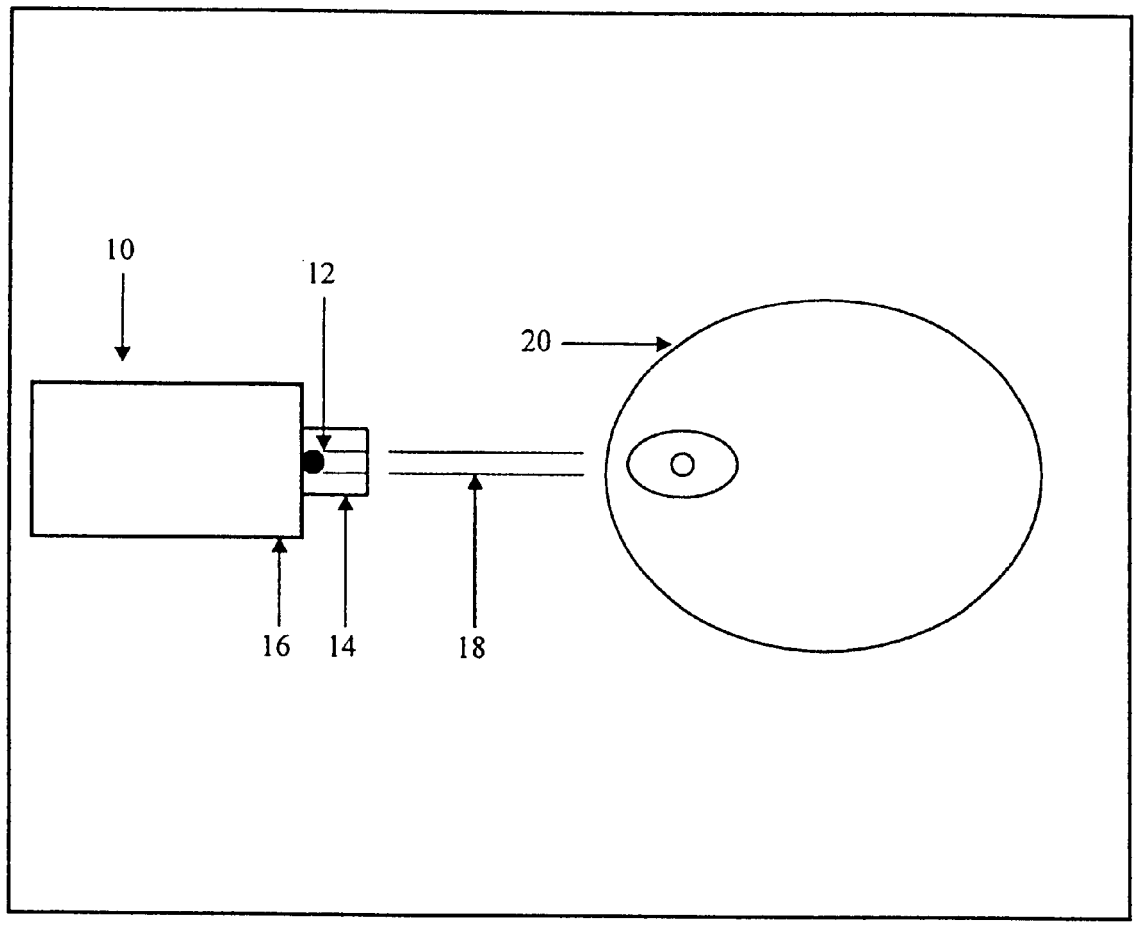
FIG. 2 is a top view showing the operation of an x-ray detector system using an embodiment of the present invention.

FIGS. 1, 2, and 3 do not show the fibula bone that is in the shadow of the tibia when exposed to the $^{109}$Cd source photon source. The incorporation of the fibula bone in an embodiment of the present invention is optional for X-ray fluorescence. The fibula bone is included in an embodiment of the present invention for in vivo measurement of radioactivity in bone.

Although not shown in this embodiment, a phantom device of the present invention could contain a trabecular bone simulant rather than a cortical bone simulant or it could contain a layer of cortical bone simulant over the trabecular bone simulant surrounding the bone marrow simulant. While it is foreseen that the tibia phantom may be the most widely used embodiment of the present invention, it is well within the scope of the art to adapt the present invention to provide a knee phantom containing a femur, tibia, fibula, and patella. It should also be readily apparent that a phantom anthropomorphically resembling any desired body structure segment containing bone could be devised based on this disclosure.

In one embodiment, the present invention provides for a reference phantom for use in calibrating the response of a spectroscopic analysis detector system, comprising:
  a. an anthropomorphic bone structure, said bone structure including:
    1. an outer bone simulant structure, said outer bone structure to be selected from the group consisting of cortical bone simulant and trabecular bone simulant; and
    2. a bone marrow simulant structure; and
  b. optionally, a muscle simulant covering.

In another embodiment, the present invention provides for a reference phantom which further contains a known amount of a contaminant being uniformly placed within the outer bone simulant structure.

Preferably, the contaminant in the reference phantom is lead.

In another embodiment, the present invention provides for a method of calibrating an x-ray fluorescence detector system. The detector system typically includes a photon source and a detector. An anthropomorphic bone structure, including an outer bone simulant structure and a bone marrow simulant structure, is placed in front of a photon beam of known energy emitted from the x-ray source and x-ray fluorescence is produced in the anthropomorphic bone structure, and measured by a detector.

In another embodiment, the present invention provides for a method of calibrating an x-ray fluorescence detector system where a muscle simulant covers the anthropomorphic bone structure.

In another embodiment, the present invention provides for a method of calibrating an x-ray fluorescence detector system where a known amount of contaminant is uniformly placed within the outer bone simulant structure of the anthropomorphic bone structure. Preferably, the contaminant is lead.

The preferred method of fabricating the phantom of the present invention comprises forming the phantom from an organic polymer and calcium material and adding the desired concentration of heavy metal. By varying the loading of the calcium compound in the resins, phantoms of various concentrations and densities can readily be fabricated. The length and width of the individual steps can be varied depending on the area of the patient's body to be measured and the detector system used.

In accordance with another aspect of the present invention there is provided a method of quantifying heavy metals using a calibration phantom composed of the heavy metal doped polymer and calcium composition. The method involves separately measuring the calibration phantom and the patient for the purpose of quantifying the patient's heavy metal concentration. Under the method of the present invention, the calibration phantom is measured and the result is compared with the individual patient. By placing the calibration phantom in the same photon beam as the patient, reference calibration measurement allow corrections and calibration of the scattering and absorption properties of the patient relative to the phantom. Each patient, having a different size, thickness, muscle-to-fat ratio, and bone content, attenuate the beam differently and thus change the effective photon beam spectrum.

DESCRIPTION OF MATERIALS

The material utilized for the outer bone simulant structure of the calibration phantoms of the present invention comprises:
  1. A low effective atomic number material (substrate);
  2. additive materials;
  3. Optionally, a contaminant; and
  4. One or more other optional ingredients The low effective atomic number material (substrate) should be approximately tissue equivalent in regard to x-ray attenuation properties, and be made up of a material which can be easily molded and fabricated into the desired geometries and which, in addition, is stable over prolonged periods of time. Generally, the substrate is a polymer. The material utilized for the calibration phantoms of the present invention further comprises additive materials to adjust the effective atomic number of the substrate which may be one or more calcium and/or potassium containing compounds.

The preferred candidate is a mixture of polyurethane combined with a calcium carbonate and heavy metals and formed into a cortical or trabecular bone shape with a bone marrow simulant.

A. Substrates

The starting materials needed to make the instant compounds are largely items of commerce or can be made by generally known methods.

Substrates in which the compounds of this invention are particularly useful are polyolefins such as polyethylene and polypropylene; polystyrene, including especially impact polystyrene; polyurethanes, ABS resins; and elastomers, e.g., butadiene rubber, EPM, EPDM, SBR and nitrile rubber.

In general polymers which can be used include:
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.
2. Mixtures of the polymers mentioned under (1), for example mixtures of polypropylene with polyisobutylene.
3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.
4. Polystyrene, poly-(p-methylstyrene).
5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.
6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.
7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.
8. Polymers which are derived from alpha, beta -unsaturated acids and derivatives thereof, such as polyacrylates and polymethacrylates, polyacrylamide and polyacrylonitrile.
9. Copolymers from the monomers mentioned under (8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.
10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.
11. Homopolymers and copolymers of cyclic ethers, such as polyalkylene glycols, polyethylene oxide, polypropylene oxide or copolymers thereof with bis-glycidyl ethers.
12. Polyacetals, such as polyoxymethylene and those polyoxymethylenes which contain ethylene oxide as comonomer.
13. Polyphenylene oxides and sulfides, and mixtures of polyphenylene oxides with polystyrene.
14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).
15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.
16. Polyureas, polyimides and polyamide-imides.
17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.
18. Polycarbonates.
19. Polysulfones, polyethersulfones and polyetherketones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low flammability.
23. Thermosetting acrylic resins, derived from substituted acrylic esters, such as epoxy-acrylates, urethane-acrylates or silicone-acrylates.
24. Alkyd resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides.
26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.
28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.
29. Aqueous emulsions of natural or synthetic rubber, e.g. natural latex or latices of carboxylated styrene/butadiene copolymers.
30. Polysiloxanes such as the soft, hydrophilic polysiloxanes described, for example, in U.S. Pat. No. 4,259,467; and the hard polyorganosiloxanes described, for example, in U.S. Pat. No. 4,355,147.
31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
32. Radiation curable compositions containing ethylenically unsaturated monomers or oligomers and a polyunsaturated aliphatic oligomer such as Santolink XI 100 (Monsanto).
33. Epoxymelamine resins such as light-stable epoxy resins crosslinked by an epoxy functional coetherified high solids melamine resin such as LSE 4103 (Monsanto).

In general, the compounds of the present invention are employed in from about 25% to about 95% by weight of the stabilized composition, although this will vary with the particular substrate and application. An advantageous range is from about 30% to about 95%, and especially 30% to about 45%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer.

In general, additional compounds of the present invention can be added to polymeric materials before, during or after the polymerization or cross-linking of said materials.

B. Additive Materials to Adjust the Effective Atomic Number

The preferred material to adjust the effective atomic number of the tissue substitute in the construction of an embodiment of the phantom bone simulant is $CaCO_3$.

Various concentrations of dipotassium hydrogen phosphate($K_2HPO_4$), potassium chloride (KCl), plaster of paris, calcium hydroxyapatite $Ca_5(PO_4)_3(OH)$, or mixtures thereof may be also used to simulate human bone x-ray absorption and scattering.

In another embodiment, the calcium material is calcium phosphate tribasic such as is manufactured by Monsanto Chemicals under the name of Tricalcium Orthophosphate ($3Ca(PO_4)_2.Ca(OH)_2 3H_2O$).

It will be recognized from this description to those skilled in the art that other materials having divergent Compton scattering, Compton absorption, and photoelectric absorption cross sections may be used in place of the X-ray absorbing and scattering additives described here. The relative quantities of such adjusted materials will, of course, have to be adjusted according to their particular absorption characteristics.

C. Contaminant Reference Materials

The present invention may include various known concentrations of heavy metals including arsenic, barium, beryllium, cadmium, chromium, cobalt, copper, iron, lead, magnesium, manganese, mercury, nickel, vanadium, and zinc.

It will, of course, be understood that the present invention is not limited only to bone heavy metal analysis systems but may contain samples having radioactive materials for calibrating detectors for other diagnostic uses.

In another embodiment, the reference materials may be composed of radioactive substances which deposit in human bone, such as uranium, plutonium, radium, americium and radioisotopes of calcium europium, strontium, phosphorus and potassium.

D. Optional Components

The resulting polymer compositions of the invention may optionally also contain various conventional additives, such as the following.

1. Antioxidants
2. UV absorbers and light stabilizers
3. Metal deactivators, for example, N,N'-diphenyloxalic acid diamide, N-salicylal-N'-salicyloylhydrazine, N,N'-bis-salicyloylhydrazine, N,N'-bis(3,5-di-tert-butyl-4-hydroxyphenylpropionyl)-hydrazine, 3-salicyloylamino-1,2,4-triazole, bis-benzylidene-oxalic acid dihydrazide.
4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.
5. Compounds which destroy peroxide, for example, esters of beta-thiodipropionic acid (e.g., the lauryl, stearyl, myristyl or tridecyl esters), mercapto-benzimidazole or the zinc salt of 2-mercaptobenzimidazole, zinc dibutyl-dithiocarbamate, dioctadecyl disulfide, pentaerythritol tetrakis-(beta-dodecylmercapto)-propionate.
6. Polyamide stabilizers, for example copper salts in combination with iodides and/or phosphorus compounds and salts of divalent manganese.
7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.
8. Nucleating agents, for example, 4-tert-butyl-benzoic acid, adipic acid, diphenylacetic acid.
9. Fillers and reinforcing agents, for example, calcium carbonate, silicates, glass fibers, asbestos, talc, kaolin, mica, barium sulfate, metal oxides and hydroxides, carbon black, graphite.
10. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The urethane material is particularly advantageous in providing a homogeneous phantom without attenuation variations across the cross section of the phantom body. Moreover, the urethane material is translucent so that any defects in the materials can be readily observed visually. Further, as described below, the physical characteristics of the urethane material can be varied to provide either rigid phantoms or flexible phantoms that can be contoured to the patient's body.

The hardness and rigidity of the phantom may be modified by changes in chemistry of the urethanes. Thus, a rigid phantom may be constructed using the urethane material whereas the urethane chemistry may be changed using conventional techniques to provide for a flexible phantom base which can be contoured to various shapes including contouring to the patient's body.

The choice of binder and stabilizer agents are largely immaterial to the X-ray absorption and scattering characteristics of the phantom material. Nevertheless, they affect the ease with which the materials may be combined and ultimate mechanical property of the material formed. The stabilizer may be a powdered polyethylene having a powder size of approximately 20 microns such as Polyethylene F microfine powder sold by Quantum Chemical Corp. of Cincinnati, Ohio.

The chemical composition, and method of making, the preferred embodiment of the present invention will now be described. The overall length and shape of the phantom depends upon the human shape being duplicated. For the preferred embodiment of the tibia phantom, the phantom is approximately 20 cm in length. As described in greater detail hereinafter, a precisely known quantity of a metal contaminant, such as lead, can be added in incremental amounts to the formulations for either the cortical or trabecular bone simulants, the bone marrow simulants, or the muscle simulants during their fabrication to produce a set of phantoms that contain a uniform or non uniform concentration of the desired heavy metal contaminant to be measured. These contaminant-containing phantoms can then be used to calibrate the response of detector systems to the particular metal contaminant being measured.

E. Cortical Bone:

The cortical bone simulant is formed from a mixture of polymers and an additive with a higher atomic number to produce a final material with a higher effective atomic number than the polymer alone.

Generally, the cortical bone simulant is composed of from about 40 wt. % to about 80 wt. % of the additive and of from about 25 wt. % to about 60 wt. % of the polymer. Preferably, the muscle simulant contains about 55 wt. % to about 60 wt. % of the additive and of from about 40 wt. % to about 50 wt. % of the polymer.

In one embodiment, the cortical bone simulant contains no heavy metal or radioisotope material for use as a blank calibration standard. In another embodiment, the cortical bone simulant contains heavy metals or radioisotope materials in known quantities to create standard calibration references.

Generally, the cortical bone simulants used to create standard calibration references contain from about 1 ppm to about 200 ppm of heavy metal or from about 0.2 nCi to about 10,000 nCi radioisotope material. Preferably, the cortical bone simulants used to create standard calibration references are composed of from about 10 wt. % to about 60 wt. % of heavy metal or from 1 nCi to about 1,000 nCi of the radioisotope material.

The typical formulation for cortical bone simulant involves approximately 58% by weight of calcium carbonate and approximately 42% by weight of polymer. Preferably, epoxy resins, commonly called polyurethane, are utilized which result in a material that has a density and mass attenuation coefficient similar to that of cortical bone, although, depending upon the contaminant being tested, and the size of the phantom, slight variations in the formulation of approximately 4% calcium carbonate to 65% calcium carbonate have been used.

The polyurethane embodiment consists of two different types of resins that are activated with a stannous octoate catalyst, viz., adiprene L-167 and LHT-240. Calcium carbonate is added to the resins in incremental quantities until a uniform thixotropic mixture is formed and then all the air that has been entrained during mixing is removed by applying a vacuum. The total mass of $CaCO_3$ added is typically 295.49 g, although other values have been added to the mixture to complete the reaction and produce a paste-like compound that is formed into the desired shape using a mold fabricated from a natural bone having the required shape.

F. Trabecular Bone:

Trabecular bone is fabricated from the same components using the same procedure as that used for cortical bone, except that the composition and density are adjusted accordingly. Generally, the trabecular bone simulant is composed of from about 15 wt. % to about 45 wt. % of the additive and of from about 30 wt. % to about 70 wt. % of polymer. Preferably, the trabecular bone simulant contains about 30 wt. % to about 35 wt. % of the additional material and of from about 65 wt. % to about 68 wt. % of polymer.

In one embodiment, the trabecular bone simulant contains no heavy metal or radioisotope material for use as a blank calibration standard. In another embodiment, the trabecular bone simulant contains heavy metals or radioisotope materials in known quantities to create standard calibration references.

Generally, the trabecular bone simulants used to create standard calibration references contain from about 1 ppm to about 200 ppm of heavy metal or from about 0.2 nCi to about 10,000 nCi radioisotope material. Preferably, the cortical bone simulants used to create standard calibration references are composed of from about 10 wt. % to about 60 wt. % of heavy metal or from 1 nCi to about 1,000 nCi of the radioisotope material.

In the preferred embodiment, the percentage of the $CaCO_3$ additive and polyurethane in samples of trabecular bone are approximately 33 and 67, respectively. The density of the trabecular bone simulant was approximately 1.4 g $cm^{-3}$. Acceptable values for these parameters may be adjusted by about 45% according to the required application.

G. Bone Marrow:

Bone marrow simulant is generally fabricated from any inert resin capable of acting as a solid support for the bone covering since, in the human subject, the composition of this compartment contains no heavy metal contaminant or radioactivity and makes no contribution to the behavior of the phantom for x-ray fluorescence or radioactivity measurements. The resin is preferably substantially free of heavy metal contaminants.

The resins to which the bone marrow simulant of the present invention can be made are preferably thermoplastic resins, thermoplastic elastomers and synthetic waxes. More preferable is at least one selected from the group consisting of polyphenylene ether resins, polyacrylic resins, polystyrene resins, polyamide resins, polyolefin resins, olefin base thermoplastic elastomers, polyurethanes and hydrocarbon base synthetic waxes.

The preferable polyolefin resin is at least one selected from the group consisting of polyethylene, polypropylene, polyurethane, ethylene-propylene copolymers and mixtures thereof Most preferably, the resin is made from polyurethane.

H. Muscle:

In yet another embodiment, a muscle simulant is placed around the cortical bone/bone marrow simulant. This embodiment produces a phantom which more closely approximates the human tissue and bone.

Generally, the muscle simulant is composed of from about 1 to about 10 wt. % of the additive and of from about 85 wt. % to about 97 wt. % of the polymer. Preferably, the muscle simulant contains about 4 wt. % to about 4.5 wt. % of the X-ray absorbing materials and of from about 95 to about 96 wt. % of the polymer.

A typical muscle simulant contains approximately 4.3% of the additive $CaCO_3$ and 95.7% polymer and produces a material having a density of approximately 1.2 g cm$^{-3}$. The values adopted for constituent materials required in these phantoms may be adjusted by about 5% to about 15% according to the required application.

While the additives calcium carbonate and polyurethane are the preferred materials for the construction of an embodiment of the phantom, other materials, such as potassium chloride or plaster of paris for the calcium carbonate and polyethylene or polystyrene for the polyurethane composition, could be used to formulate the phantom, but would not be the recommended materials because the phantom would not exhibit the desired attenuation coefficient or density.

In this disclosure, it should be understood that other embodiments of the invention are possible and that, depending upon the bone section in questions, the contaminant to be studied, and the photon energy of the x-ray source, various modifications and changes can be made to the invention, within the scope of the attached claims, which define the true scope of the invention.

One or more additional components can be added to the materials so long as the final embodiment can be formed into the desired shape, and has the same effective atomic number and mass attenuation coefficient as natural human tissue.

It should be understood by the reader that the choice of spectroscopic analysis, defined herein as x-ray fluorescence and gamma spectrometry, depends on the nature of the contaminant being tested, and that such things as the source of radiation and its intensity will also vary, and that such variances are well known to those skilled in the art.

We claim:

1. A reference phantom for use in calibrating the response of a spectroscopic analysis detector system, comprising an anthropomorphic bone structure, said bone structure comprising:
    an outer bone simulant component selected from a group consisting of cortical bone simulant and trabecular bone simulant;
    an inner bone marrow simulant component encased by the outer bone simulant; and
    a muscle simulant component disposed around the outer bone simulant;
    wherein the components each have substantially the same effective atomic number and mass attenuation coefficient as the corresponding natural human tissues.

2. The reference phantom as recited in claim 1, wherein the components comprise a low effective atomic number polymer substrate and an additive material capable of adjusting the effective atomic number and mass attenuation coefficient of the components.

3. The reference phantom as recited in claim 2, wherein the additive material effects a characteristic of the component selected from the group consisting of Compton scattering, Compton absorption, photoelectric absorption, X-ray absorption and X-ray scattering.

4. The reference phantom as recited in claim 3, wherein the outer bone simulant further comprises a known amount of a contaminant uniformly placed within the outer bone simulant.

5. The reference phantom as recited in claim 4, wherein the bone structure is anthropomorphically shaped to resemble a limb of a human.

6. The reference phantom as recited in claim 5, wherein the polymer is selected from the group consisting of polyethylene, polypropylene, polyisobutylene, polybutene-1, polymethylpentene-1, polyisoprene, polybutadiene, cyclopentene, norbornene, polystyrene, poly-(p-methylstyrene, graft copolymers of styrene, halogen-containing polymers, polymers which are derived from alpha, beta -unsaturated acids, polymers which are derived from unsaturated alcohols and amines, or acyl derivatives thereof or acetals thereof, homopolymers and copolymers of cyclic ethers, polyacetals, polyphenylene oxides and sulfides, polyurethanes, polyamides, polyureas, polyimides and polyamide-imides, polyesters, polycarbonates, polysulfones, polyethersulfones, polyetherketones, drying and non-drying alkyd resins, unsaturated polyester resins, thermosetting acrylic resins, natural polymers, aqueous emulsions of natural or synthetic rubber, polysiloxanes, radiation curable compositions, epoxymelamine resins, and derivatives, copolymers, and mixtures thereof.

7. The reference phantom as recited in claim 6, wherein the polymer is polyurethane.

8. The reference phantom as recited in claim 5, wherein the limb is the midshaft of the lower leg of a human.

9. The reference phantom as recited in claim 5, wherein the contaminant is a heavy metal selected from the group consisting of arsenic, barium, beryllium, cadmium, chromium, cobalt, copper, iron, lead, magnesium, manganese, mercury, nickel, vanadium, zinc, and mixtures thereof.

10. The reference phantom as recited in claim 9, wherein the contaminant is lead.

11. The reference phantom as recited in claim 5, wherein the contaminant is a radioactive material selected from the group consisting of uranium, plutonium, radium, americium, radioisotopes of calcium, europium, strontium, phosphorus and potassium, and mixtures thereof.

12. The reference phantom as recited in claim 11, wherein the contaminant is a radioactive strontium.

13. The reference phantom as recited in claim 3, wherein the outer bone simulant further comprises one or more additional ingredients.

14. The reference phantom as recited in claim 2, wherein the additive material is selected from the group consisting of calcium carbonate, dipotassium hydrogen phosphate, potassium chloride, plaster of paris, calcium phosphate, calcium phosphate tribasic, calcium hydroxyapatite, and mixtures thereof.

15. The reference phantom as recited in claim 14, wherein the additive material is a calcium carbonate.

16. A method of calibrating an x-ray fluorescence detector system, said system including a photon source and a detector, comprising:
    placing an anthropomorphic bone structure in front of a photon beam source of known energy emitted, said bone structure comprising:
    an outer bone simulant component selected from a group consisting of cortical bone simulant and trabecular bone simulant;

an inner bone marrow simulant component encased by the outer bone simulant; and a muscle simulant component disposed around the outer bone simulant component;

wherein the components each have substantially the same effective atomic number and mass attenuation coefficient as the corresponding natural human tissues;

producing x-rays and photons by x-ray fluorescence in the anthropomorphic bone structure;

measuring the photons and x-rays produced with the detector; and calibrating the x-ray fluorescence detector system to the measured photons and x-rays.

17. The method as recited in claim 16, wherein the components comprise a low effective atomic number polymer substrate and an additive material capable of adjusting the effective atomic number and mass attenuation coefficient of the components.

18. The method as recited in claim 17, further comprising a known amount of contaminant uniformly placed within the outer bone simulant.

19. The method as recited in claim 18, wherein the bone structure is anthropomorphically shaped to resemble a limb of a human.

20. The method as recited in claim 19, wherein the contaminant is a heavy metal selected from the group consisting of arsenic, barium, beryllium, cadmium, chromium, cobalt, copper, iron, lead, magnesium, manganese, mercury, nickel, vanadium, zinc, and mixtures thereof.

21. The method as recited in claim 19, wherein the contaminant is a radioactive material selected from the group consisting of uranium, plutonium, radium, americium, radioisotopes of calcium, europium, strontium, phosphorus and potassium, and mixtures thereof.

22. The method as recited in claim 19, wherein the method further comprises the steps of:

placing a human limb to be measured in front of the photon beam source;

producing x-rays and photons by x-ray fluorescence in the limb;

measuring the photons and x-rays produced with the detector; and determining the amount of contaminant in the limb by correlating the measured photons and x-rays from the limb to the measured photons and x-rays of the anthropomorphic bone structure.

* * * * *